(12) United States Patent
Al-Zahrani et al.

(10) Patent No.: US 9,782,754 B2
(45) Date of Patent: Oct. 10, 2017

(54) ALKANE DEHYDROGENATION CATALYST AND PROCESS FOR ITS PREPARATION

(71) Applicant: Saudi Basic Industries Corporation, Riyadh (SA)

(72) Inventors: Abdulrahim Al-Zahrani, Jeddah (SA); Lachezar A. Petrov, Jeddah (SA); Mohammad Daous, Jeddah (SA); Mohammad Umar, Riyadh (SA); Mohammed Al-Hazmi, Riyadh (SA); Yahia Al-Hamed, Jeddah (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 157 days.

(21) Appl. No.: 14/416,803

(22) PCT Filed: Jul. 26, 2013

(86) PCT No.: PCT/IB2013/056149
§ 371 (c)(1),
(2) Date: Jan. 23, 2015

(87) PCT Pub. No.: WO2014/016810
PCT Pub. Date: Jan. 30, 2014

(65) Prior Publication Data
US 2015/0202599 A1    Jul. 23, 2015

(30) Foreign Application Priority Data

Jul. 26, 2012    (EP) ..................................... 12005440

(51) Int. Cl.
| | | |
|---|---|---|
| *B01J 23/62* | (2006.01) | |
| *B01J 37/06* | (2006.01) | |
| *B01J 37/08* | (2006.01) | |
| *B01J 23/36* | (2006.01) | |
| *B01J 35/10* | (2006.01) | |
| *B01J 37/02* | (2006.01) | |
| *C07C 5/333* | (2006.01) | |
| *B01J 21/04* | (2006.01) | |
| *B01J 35/00* | (2006.01) | |

(52) U.S. Cl.
CPC ............. *B01J 23/626* (2013.01); *B01J 21/04* (2013.01); *B01J 23/36* (2013.01); *B01J 35/0006* (2013.01); *B01J 35/1014* (2013.01); *B01J 35/1019* (2013.01); *B01J 37/0201* (2013.01); *B01J 37/0215* (2013.01); *B01J 37/06* (2013.01); *B01J 37/08* (2013.01); *C07C 5/3337* (2013.01); *C07C 2521/04* (2013.01); *C07C 2523/02* (2013.01); *C07C 2523/06* (2013.01); *C07C 2523/14* (2013.01); *C07C 2523/42* (2013.01); *C07C 2523/62* (2013.01); *Y02P 20/52* (2015.11)

(58) Field of Classification Search
CPC . B01J 23/58; B01J 23/60; B01J 23/626; B01J 23/36; B01J 23/06; B01J 23/14; B01J 35/006; B01J 35/1014; B01J 35/1019; B01J 37/0201; B01J 37/0215; B01J 37/0234; B01J 37/06; B01J 37/08; B01J 37/14; B01J 21/04; B01J 21/063; B01J 21/066; C07C 2521/04; C07C 2523/02; C07C 2523/06; C07C 2523/14; C07C 2523/42; C07C 2523/62
USPC ......... 502/325, 328, 329, 332–334, 339–343
See application file for complete search history.

(56) References Cited

U.S. PATENT DOCUMENTS

| | | | |
|---|---|---|---|
| 4,210,561 A * | 7/1980 | Antos | ..................... B01J 23/462 502/226 |
| 4,366,091 A * | 12/1982 | Antos | .................. B01J 23/6567 502/174 |
| 4,914,075 A | 4/1990 | Bricker et al. | |
| 5,430,220 A | 7/1995 | Khare et al. | |
| 5,877,369 A | 3/1999 | Wu et al. | |
| 6,576,804 B1 | 6/2003 | Heineke et al. | |
| 2002/0103079 A1 | 8/2002 | Lepeltier et al. | |
| 2003/0191351 A1 | 10/2003 | Voskoboynikov et al. | |
| 2003/0202934 A1 | 10/2003 | Voskoboynikov et al. | |
| 2005/0033101 A1 | 2/2005 | Voskoboynikov et al. | |

(Continued)

FOREIGN PATENT DOCUMENTS

| | | |
|---|---|---|
| CN | 101015802 A | 8/2007 |
| CN | 101066532 A | 11/2007 |

(Continued)

OTHER PUBLICATIONS

Machine Translation of DE19858747; Date of Publication: Dec. 18, 1998; 6 pages.
Hongfa, Zhu arid Liu Lizhi, eds., Catalyst Preparation and Application of Technology, China Petrochemical Press, Jun. 2011, 4 Pages.
Machine Translation of Catalyst Preparation and Application of Technology; Jun. 2011, 3 Pages.

(Continued)

*Primary Examiner* — Patricia L Hailey
(74) *Attorney, Agent, or Firm* — Cantor Colburn LLP

(57) ABSTRACT

The invention relates to a catalyst composition comprising (a) a metal M selected from the group consisting of platinum (Pt), palladium (Pd), rhodium (Rh), rhenium (Re), ruthenium (Ru) and iridium (Ir), (b) tin (Sn), (c) zinc (Zn), (d) alkaline earth metal and (e) a porous metal oxide catalyst support, wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support. Furthermore, the invention also relates to a process for the preparation of said catalyst composition and its use in non-oxidative dehydrogenation of an alkane, preferably propane.

18 Claims, No Drawings

(56) References Cited

U.S. PATENT DOCUMENTS

| | | | |
|---|---|---|---|
| 2008/0051618 A1* | 2/2008 | Kim | B01J 23/62 585/431 |
| 2009/0105511 A1* | 4/2009 | Okada | B01J 21/04 585/434 |
| 2009/0325791 A1 | 12/2009 | Pan et al. | |
| 2010/0236985 A1 | 9/2010 | Luo et al. | |
| 2010/0314294 A1 | 12/2010 | Siskin et al. | |
| 2011/0038763 A1 | 2/2011 | Hechler et al. | |
| 2011/0045969 A1 | 2/2011 | Vajda et al. | |
| 2015/0209759 A1 | 7/2015 | Al-Hazmi et al. | |

FOREIGN PATENT DOCUMENTS

| | | |
|---|---|---|
| CN | 101125298 A | 2/2008 |
| CN | 101138734 A | 3/2008 |
| CN | 101164690 A | 4/2008 |
| CN | 101380587 A | 3/2009 |
| CN | 101411978 A | 4/2009 |
| CN | 101513613 A | 8/2009 |
| CN | 101773850 A | 7/2010 |
| CN | 101898138 B | 12/2010 |
| CN | 101898131 B | 5/2012 |
| DE | 19858747 A1 | 12/1998 |
| EP | 0328507 a1 | 8/1989 |
| EP | 0328507 | 10/1989 |
| EP | 0486993 B1 | 5/1995 |
| EP | 1598411 A1 | 11/2005 |
| EP | 1048348 B1 | 7/2007 |
| EP | 2689841 A1 | 1/2014 |
| GB | 1295933 | 11/1972 |
| JP | 10180101 | 7/1998 |
| JP | 10182505 | 7/1998 |
| KR | 20100078460 A | 7/2010 |
| WO | 9429021 A1 | 12/1994 |
| WO | 0147842 A1 | 7/2001 |
| WO | 0152984 A1 | 7/2001 |
| WO | 03013728 A2 | 2/2003 |

OTHER PUBLICATIONS

Nawaz, Z. "SAPO-34 supported bi-metallic (Pt—Sn-based) novel catalyst for Light Alkane Dehydrogenation to Propylene", Patent Application PK140812/2010.
English Abstract of CN101164690(A); Date of Publication: Apr. 23, 2008; 1 Page.
English Abstract of CN101773850(A); Date of Publication: Jul. 14, 2010; 2 Pages.
English Abstract of CN1121844; Date of Publication: May 8, 1996; 1 Page.
Machine Translation of JP10-180101; Date of Publication: Jul. 7, 1998; 8 Pages.
International Search Report & Written Opinion; International Publication No. PCT/IB2013/056149; Internation Filing Date Jul. 26, 2013; dated Dec. 2, 2013; 10 pages.
European Search Report for Application No. 12005440.8; dated Jan. 23, 2013; 6 Pages.
Aguilar-Rios et al.; "Hydrogen Interactions and Catalytic Properties of Platinum-tin Supported on Zinc Aluminate"; Applied Catalysis A: General 127; pp. 65-75; (1995).
Aguilar-Rios et al.; "Propane Dehydrogenation Activity of Pt and Pt—Sn Catalysts Supported on Magnesium Aluminate: Influence of Steam and Hydrogen"; Catalysis Letters; 60; pp. 21-25; (1999).
Bednarova et al.; "Effect of Support on the Size and Compositions of Highly Dispersed Pt—Sn Particles"; Journal of Catalysis; 211; pp. 335-346; (2002).
Chen et al.; "Isotopic Tracer Studies of Reaction Pathways for Propane Oxidative Dehydrogenation on Molybdenum Oxide Catalysts"; J. Phys. Chem. B; 105; pp. 646-653; (2001).
Duan et al.; "Effect of Sodium Addition of PtSn/A1SBA-15 on Catalytic Properties in Propane Dehydrogenation"; Catal Lett; 141; pp. 120-127; (2011).
Nawaz et al.; "Hydrothermal Study of Pt—Sn-based SAPO-34 Supported Novel Catalyst Used for Selective Propane Dehydrogenation to Propylene"; Journal of Industrial and Engineering Chemistry; 16; pp. 774-784; (2010).
Rennard et al.; "The Role of Sulfur in Deactivation of Pt/MgAl2O4 for Propane Dehydrogenation"; Journal of Catalysis; 98(2); pp. 235-244; (1986).
Sun et al.; "Synthesis and Characterization of a New Catalyst Pt/Mg(Ga)(Al)O for Alkane Dehydrogenation"; Journal of Catalysis; 274; pp. 192-199; (2010).
Waku et al.; "Catalytic Dehydrogenation of Alkanes on Pt/Na—[Fe]ZSM5 and Staged O2 Introduction for Selective H2 Removal"; Journal of Catalysis; 222; pp. 481-492; (2004).
Weirauch, et al.; HPImpact: Propylene Demand to Grow 4.7%/yr: Ethylene Expansions Required; Hydrocarbon Processing; 83; pp. 23-25; (2004).
Zhang et al.; "Effect of K Addition on Catalytic Performance of PtSn/ZSM-5 Catalyst for Propane Dehydrogenation"; Catalysis Letters; 135; pp. 76-82; (2010).

* cited by examiner

ALKANE DEHYDROGENATION CATALYST AND PROCESS FOR ITS PREPARATION

CROSS REFERENCE TO RELATED APPLICATIONS

This application is a 371 of Interational Application No. PCT/IB2013/056149, filed Jul. 26, 2013, which claims priority to European Application No. 12005440.8, filed Jul. 26, 2012, both of which are hereby incorporated by reference in their entirty.

The invention relates to a catalyst composition suitable for the non-oxidative dehydrogenation of alkanes, to a process for the preparation thereof and to a non-oxidative dehydrogenation process using said catalyst composition and to the use of said catalyst composition in the non-oxidative dehydrogenation of alkanes, preferably of propane.

Alkenes, such as propylene are basic chemicals which are used in industrial processes such as the production of polypropylene, acrylic acid, acrylonitrile, cumene and many others. The demand for alkenes, such as propylene increases annually. Therefore, there is a continuing need to improve the yield of processes for the preparation of alkenes. One such process for the preparation of alkenes, such as propylene is the non-oxidative catalytic dehydrogenation of alkanes, such as propane.

Such a process is for example described in EP0328507A1. EP0328507 discloses a process for the catalytic dehydrogenation of propane, in the presence of hydrogen in a molar ratio of from 0.05 to 0.5 mole of hydrogen per mole of propane over a catalyst consisting of an alumina support containing at least one metal of the platinum group together with a co-catalyst and a promoter, which comprises the step of passing the feed to be dehydrogenated onto a catalyst containing from 0.2 to 1% by weight of platinum, from 0.15 to 1% by weight of tin as co-catalyst and from 0.8 to 2% by weight of potassium as promoter, said catalyst being obtained by submitting the alumina support containing the co-catalyst and calcined at a temperature comprised between 450 and 550° C.,

- to a first treatment with a platinum compound, said first treatment being followed by a calcination in air and a reduction in the presence of hydrogen at a temperature comprised between 450 and 550° C.;
- then to an intermediate treatment to deposit potassium, said intermediate treatment being followed by a calcination at a temperature comprised between 380 and 550° C.,
- and finally to a second treatment with a platinum compound, said second treatment being followed by a calcination at a temperature not exceeding 525° C., the dehydrogenation being carried out in the presence of said catalyst at a temperature comprised between 530° C. and 650° C., a pressure comprised between 0.5 and 3 atm. and a weight hourly space velocity comprised between 1 and 10.

Also JP10180101 describes a process for the non-oxidative catalytic dehydrogenation of an alkane in the presence of hydrogen. The catalyst used comprises a $ZnO/Al_2O_3$ support, wherein the amount of ZnO is in the range of 5-50 weight %. In the examples the weight ratio of $ZnO:Al_2O_3$ is 30:70 or 44:55. Further the catalyst comprises the elements Pt in an amount of 0.05 to 1.5 wt %, Sn in an amount of 0.5 to 10 wt % and an alkaline metal in an amount of 0.01 to 10 wt %.

It is the aim of the invention to provide an improved process for the catalytic non-oxidative dehydrogenation of alkanes.

This object is achieved by the provision of a catalyst composition comprising
- (a) a metal M selected from the group consisting of platinum (Pt), palladium (Pd), rhodium (Rh), rhenium (Re), ruthenium (Ru) and iridium (Ir)
- (b) tin (Sn)
- (c) zinc (Zn)
- (d) alkaline earth metal and
- (e) a porous metal oxide catalyst support, wherein the amount of each of elements (a), (b), and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support.

The catalyst composition of the invention is suitable for the non-oxidative dehydrogenation of an alkane, in particular for the non-oxidative dehydrogenation of propane to propene as it can form propene from propane in a high yield and with a high selectivity.

By using the catalyst composition of the invention in non-oxidative dehydrogenation of alkanes and in particular of propane, one or more of the following additional advantages may also be achieved:
1) the amount of cokes formed on the catalyst composition may be reduced
2) the amount of ethylene obtained as a side product (as compared to the total side product) may be increased, thereby increasing the amount of valuable products formed and/or
3) the active surface of the catalyst in the catalyst composition may be increased.

As used herein, the term "catalyst composition" is understood to mean a composition consisting of the catalyst (active phase) and any other suitable components such as a catalyst binder. The catalyst composition of the invention is for example suitable for the non-oxidative dehydrogenation of an alkane and for example particularly suitable for the non-oxidative dehydrogenation of propane.

In the catalyst composition of the invention, the metal M is selected from the group consisting of platinum (Pt), palladium (Pd), rhodium (Rh), rhenium (Re), ruthenium (Ru) and iridium (Ir). Preferably, the metal M is platinum (Pt)

In the catalyst composition of the invention, the metal M is preferably present in an amount of at least 0.1 wt %, for example at least 0.5 wt % based on the porous metal oxide catalyst support and/or at most 5 wt %, for example at most 2 wt % based on the porous metal oxide catalyst support. For example, the amount of metal Ml is in the range of from 1 to 5 wt % based on the porous metal oxide catalyst support or in the range of from 0.5 to 2 wt % based on the porous metal oxide catalyst support.

In the catalyst composition of the invention, tin (Sn) is preferably present in an amount of at least 0.1 wt %, for example at least 0.5 wt % based on the porous metal oxide catalyst support and/or at most 5 wt %, for example at most 2 wt % based on the porous metal oxide catalyst support. For example, the amount of tin (Sn) is in the range of from 1 to 5 wt % based on the porous metal oxide catalyst support or in the range of from 0.5 to 2 wt % based on the porous metal oxide catalyst support.

In the catalyst composition of the invention, zinc (Zn) is preferably present in an amount of at least 0.1 wt %, for example at least 0.5 wt % based on the porous metal oxide catalyst support and/or at most 2 wt % based on the porous metal oxide catalyst support. For example, the amount of zinc (Zn) is in the range of from 0.1 to 2 wt % based on the porous metal oxide catalyst support or in the range of from 0.5 to 2 wt % based on the porous metal oxide catalyst support.

In the catalyst composition of the invention, the alkaline earth metal is preferably present in an amount of at least 0.1 wt %, for example at least 0.5 wt % based on the porous metal oxide catalyst support and/or at most 5 wt %, for example at most 2 wt % based on the porous metal oxide catalyst support. For example, the amount of the alkaline earth metal is in the range of from 1 to 5 wt % based on the porous metal oxide catalyst support or in the range of from 0.5 to 2 wt % based on the porous metal oxide catalyst support.

Preferably, the alkaline earth metal is selected from the group consisting of magnesium (Mg), calcium (Ca) and strontium (Sr). More preferably, the alkaline earth metal is calcium (Ca).

Examples of porous metal oxide catalyst supports are known to the person skilled in the art and include but are not limited to γ-alumina (γ-$Al_2O_3$), titania ($TiO_2$), ceria ($CeO_2$), zirconia ($ZrO_2$) and mixtures thereof. Preferably, the catalyst composition of the invention comprises γ-alumina (γ-$Al_2O_3$).

The porous metal oxide catalyst support does not include zeolite supports.

The porous metal oxide catalyst support preferably has a BET surface area of 50-500 $m^2/g$., for example a BET surface area of at least 50, for example at least 100, for example at least 150 and/or at most 350, for example at most 250 $m^2/g$, for example a BET surface area of 150 to 250 $m^2/g$.

As used herein, the BET surface area is determined by $N_2$ adsorption techniques (ASTM D-3663-03, ASTM International, October 2003).

In a first special embodiment, the invention relates to catalyst composition comprising
  (a) platinum (Pt)
  (b) tin (Sn)
  (c) zinc (Zn)
  (d) magnesium (Mg), calcium (Ca) or strontium (Sr) and
  (e) a porous metal oxide catalyst support,
wherein the amount of each of elements (a), (b) and (d) is independently chosen in the range of from 0.1 to 5 wt. % based on the porous metal oxide catalyst support, preferably in the range of from 0.5 to 2 wt %, and wherein the amount of element (c) is chosen in the range of from 0.1 to 2 wt %, preferably in the range of from 0.5 to 2 wt %, based on the porous metal oxide catalyst support.

In a second special embodiment, the invention relates to a catalyst composition comprising
  (a) platinum (Pt)
  (b) tin (Sn)
  (c zinc (Zn)
  (d) calcium (Ca) and
  (e) a porous metal oxide catalyst support, preferably γ-alumina
wherein the amount of each of elements (a), (b) and (d) is independently chosen in the range of from 0.1 to 5 wt. %, preferably in the range of from 0.5 to 2 wt %, based on the porous metal oxide catalyst support and wherein the amount of element (c) is chosen in the range of from 0.1 to 2 wt. %, preferably in the range of from 0.5 to 2 wt %, based on the porous metal oxide catalyst support.

In these special embodiments of the invention, platinum is preferably the only metal M present in the catalyst compositions.

Alternatively or also, preferably in these special embodiments of the invention, magnesium, calcium or strontium is the only alkaline earth metal present in the catalyst composition.

In another aspect, the invention relates to a process for the preparation of a catalyst composition according to the invention comprising the steps of
  (a) depositing the metal M, Sn, Zn and the alkaline earth metal on the porous metal oxide catalyst support to obtain a catalyst precursor and
  (b) subjecting the catalyst precursor to calcination in an environment comprising oxygen to obtain a catalyst.

With 'depositing' is meant herein any technique that can place the metal M, Sn, Zn and the alkaline earth metal on the porous metal oxide catalyst support, such as for example impregnation precipitation, deposition-precipitation, co-precipitation, incipient wetness impregnation or a combination thereof.

Therefore, the invention also relates to a process according to the invention, wherein step (a) comprises the steps of
  (a1) contacting the porous metal oxide catalyst support with a solution comprising a salt of the metal M, a salt of tin (Sn), a salt of zinc (Zn) and a salt of the alkaline earth metal, and subsequently
  (a2) evaporating the liquid in said solution to prepare a modified slurry and optionally
  (a3) washing the modified slurry with a solvent to obtain the catalyst precursor.

It has been found that when the catalyst in the catalyst composition of the invention is prepared by depositing the metal M, Sn, Zn and the alkaline earth metal using a single solution comprising a salt of the metal M, a salt of ruthenium (Ru), a salt of iridium (Ir) and a salt of the alkaline earth metal, the catalyst provides improved catalytic properties, such as for example selectivity for propane, yield of propene and/or less deposition of carbon on the catalyst during the non-oxidative dehydrogenation.

Furthermore, when preparing the catalyst composition of the second special embodiment using a single salt solution, in the conversion of propane to propene, the amount of ethylene produced may be increased, thereby increasing the amount of valuable products formed in the non-oxidative dehydrogenation of propane.

Therefore, the invention also relates to a catalyst (composition) of the invention wherein the catalyst composition is obtained or obtainable by the process of the invention using a single salt solution, that is the process wherein step (a) comprises the steps of
  (a1) contacting the porous metal oxide catalyst support with a solution comprising a salt of the metal M, a salt of tin (Sn), a salt of zinc (Zn) and a salt of the alkaline earth metal.

In particular, the invention also relates to a catalyst composition comprising
  (a) a metal M selected from the group consisting of platinum (Pt), palladium (Pd), rhodium (Rh), rhenium (Re), ruthenium (Ru) and iridium (Ir)
  (b) tin (Sn)
  (c) zinc (Zn)
  (d) alkaline earth metal and
  (e) a porous metal oxide catalyst support,
wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support, wherein the catalyst composition is obtained or obtainable by a process comprising the steps of (f) depositing the metal M, Sn, Zn and the alkaline earth metal on the porous metal oxide catalyst support to obtain a catalyst precursor and (g) subjecting the catalyst precursor to calcination in an environment comprising oxygen to obtain a catalyst, wherein step (a) preferably comprises the steps of (a1) contacting the porous metal oxide catalyst support with a solution comprising a salt of the metal M, a salt of tin (Sn), a salt of zinc (Zn) and a salt of the alkaline earth metal, and subsequently (a2) evaporating the liquid in said solution to prepare a modified slurry and optionally (a3) washing the modified slurry with a solvent to obtain the catalyst precursor.

The salt solution(s) used to deposit the metal M, Sn, Zn and the alkaline earth metal on the porous metal oxide catalyst support preferably have a pH in the range from 2 to 10, preferably from 4 to 7.5.

The modified slurry may be dried before washing the modified slurry with the solvent.

The solvent may be any solvent that is suitable for removal of the anions. For example, water may be used.

Before subjecting the catalyst precursor to calcination in an environment comprising oxygen, the catalyst precursor may (also) be dried.

Drying of the modified slurry and/or of the catalyst precursor may be performed by subjecting the modified slurry and/or the catalyst precursor to a temperature of 600-300° C. for example a time period from 0.5 to 6 hours.

In principle, any salt of the metal M, a salt of tin (Sn), a salt of zinc (Zn) and a salt of the alkaline earth metal, that is soluble in the selected solvent that is used in the solution comprising a salt of the metal M, a salt of tin (Sn), a salt of zinc (Zn) and a salt of the alkaline earth metal may be used to modify the zinc and/or manganese aluminate. For example, suitable salts may be in the form of acetate, oxalate, nitrate, chloride, carbonate, and bicarbonate.

Preferably, one or more of the salts in the solution comprising a salt of the metal M, a salt of tin (Sn), a salt of zinc (Zn) and a salt of the alkaline earth metal are chloride salts, preferably all salts in said solution are chloride salts.

In case all salts in said solution are chloride salts, the resulting modified slurry may be washed with deionized water until a standard silver nitrate test for the presence of Cl⁻ in the filtrate water is negative.

For example, the salt of the metal M, for example platinum may be a chloride salt of the metal M, for example platinum chloride.

For example, the salt of tin, may be tin chloride.

For example, the salt of zinc may be zinc chloride. For example, the salt of the alkaline earth metal may be a chloride salt of the alkaline earth metal, for example calcium chloride.

Step (b) of the process of the invention, is preferably performed by subjecting the catalyst precursor to calcination in an environment comprising oxygen at a temperature from 100 to 650°, for example a temperature from 400 to 650° C., for example at a time from 1 to 6 hours.

The environment comprising oxygen may for example be achieved using an oxygen or air stream during the calcination.

In another aspect, the invention relates to a process for producing an alkene by non-oxidative dehydrogenation of an alkane comprising the step of contacting a feed stream comprising the alkane with the catalyst composition of the invention to form the alkene.

In the framework of the invention, with alkane is meant a hydrocarbon of formula $C_{2H2n+2}$. For example, the alkane can have from 2 to 12, preferably from 2 to 4 carbon atoms per molecule. For example, the alkane may be propane, butane, pentane, hexane, heptane, octane, nonane, decane or a mixture thereof. Preferably, the alkane is propane.

Examples of alkenes that may be produced in the process of the invention include but are not limited to propene (also referred to herein as propylene) and ethylene (also referred to herein as ethene) and butene.

The alkane may be used in its pure form, but may also be present in a feed stream of a mixture of alkanes or in a feed stream of alkane (also referred to herein as alkane feed stream) with an inert gas, such as $N_2$. Preferably, the alkane is present in a feed stream that predominantly comprises one alkane species.

Accordingly, it is preferred that the alkane comprised in the feed stream consists of at least 75 mol % of only one alkane species, more preferably of at least 85 mol % of only one alkane species, even more preferably of at least 90 mol % of only one alkane species, particularly preferably of at least 95 mol % of only one alkane species and most preferably of at least 98 mol % of only one alkane species.

Preferably, the total amount of alkane in the feed stream is at least 98 wt %, preferably at least 99 wt %, for example at least 99.5 wt %, for example at least 99.7 wt %, for example 99.9 wt % based on the total feed stream. Small amounts of olefins (for example from 0.1 to 0.5 wt % based on the total feed stream) may be present in the feed stream.

The feed stream may also comprise hydrogen. For example, the molar ratio of hydrogen to alkane in the feed stream may be in the range from about 1:6 to 0:1.

The feed stream may also comprise an inert gas diluent. The inert gas diluent may be chosen from the group of helium, nitrogen, and mixtures thereof, preferably nitrogen. For example, the molar ratio of alkane to inert gas diluent may be in the range from about 1:10 to about 1:1.

As used herein, the term "non-oxidative dehydrogenation" is understood to mean that the dehydrogenation proceeds substantially in the absence of an oxidizing agent, such as oxygen, i.e. the amount of oxidizing agent in a feed stream comprising the alkane is at most 1 vol % based on the feed stream.

The process of the present invention is performed at conditions suitable for high conversion of an alkane to an alkene. Such conditions are known by the person skilled in the art. Optimal conditions can easily be determined by the person skilled in the art using routine experimentation.

The step of contacting the feed stream comprising the alkane with the catalyst composition of the invention may for example be performed in a reactor at a temperature from 400 to 650° C. Preferably, the step of contacting the feed stream comprising the alkane with the catalyst composition of the invention is performed at a temperature of from 400 to 650, preferably at a temperature from 550 to 650° C., for example at a temperature of at most 575° C., for example at a temperature from 575 to 625° C. A lower temperature has the advantage that the energy required for the non-oxidative dehydrogenation is also lower.

The pressure within the reactor in which the non/oxidative dehydrogenation is performed preferably lies within a range of from 5 kilopascals (KPa) to 505 kilopascals, more preferably from 40 KPa to 80 KPa. For example, the pressure is 0.01-0.3 MPa.

The gas hourly space velocity (GHSV), that is the flow rate at which the feed stream comprising the alkene is fed to the reactor in which the alkane is contacted with the catalyst composition of the invention is for example in the range from 1500 to 6000, for example around $3800h^{-1}$.

GHSV is the ratio of the rate at which the feed stream comprising the alkane is fed to the reactor (in volume at standard pressure (101 KPa) per hour divided by the volume of catalyst composition at 101 KPa; and is thus inversely related to contact time.

The weight hourly space velocity (WHSV), that is the ratio of the weight of the alkane which comes in contact with a given weight of catalyst per unit time, is for example in the range from 0.1 to 10 $hour^{-1}$, for example the weight hourly space velocity is 0.1 to 1 $hour^{-1}$.

By contact time is meant the period of time during which the alkane feed stream is in contact with the catalyst composition.

Preferably the step of contacting the feed stream comprising the alkane with the catalyst composition of the invention (the non-oxidative dehydrogenation) is performed at a temperature of from 400 to 650° C., a weight hourly space velocity of 0.1-1 $hour^{-1}$ and/or a pressure of 0.01-0.3 MPa.

The GHSV indicates that there is a certain rate at which the feed stream is fed to the reactor in which the feed stream is contacted with the catalyst composition of the invention. The total length of time in which the feed stream is fed to the reactor is known as the "Time-on-Stream (TOS)." For example the TOS for a catalyst composition according to the invention during which time the catalyst composition maintains its activity in terms of a high conversion and high selectivity for an alkene, for example propylene, ranges from for example 50 to 100.

The step of contacting the alkane with the catalyst composition of the invention may be performed in any suitable reactor, as known to a skilled man, for example in a fixed bed or moving bed reactor.

In another aspect, the invention relates to use of the catalyst composition of the invention in a non-oxidative dehydrogenation of an alkane.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will now be elucidated by way of the following examples without however being limited thereto.

EXAMPLES

Example 1

Preparation of Pt—Sn—Ca—Zn/γ-$Al_2O_3$ Catalyst (Catalyst A)

5 g of γ-$Al_2O_3$ was dried at 120° C. for 2 hours. 0.0885 g of $PtCl_4$ was dissolved in 20 ml of deionized (DI) water. 0.0965 g of $SnCl_2$ was dissolved in 15 ml ethanol. 0.1450 g of $CaCl_2$ was dissolved in 10 ml of DI water. 0.1041 g of $ZnCl_2$ was dissolved in 10 ml of DI water. It was assured that the solutions of all salts were transparent and that there was no suspension at all.

The temperature of the water bath was set to 65° C. The evaporating flask of Rotavapor was filled up with DI water in a volume of 200 ml minus the volume of the salt solutions. When the temperature became stable at 65° C., all solutions prepared were added to the evaporating flask to obtain a total solution volume of 200 ml. The preheated support (γ-$Al_2O_3$ at a temperature of about 65° C.) was added to the flask and the solution was kept on rotation at 65° C. for 3.5 hours. Then the solution was evaporated under vacuum until only solid slurry was left.

The slurry was then dried for 2 hours at 120° C. in the oven. The dried catalyst mass was then washed with hot water to remove chloride ions. An $AgNO_3$ test was used to ensure the complete removal of chlorides. The washed catalyst was again dried for 2 hours at 120° C. and was then calcined at a temperature of 600° C. for 6 hours. The calcination temperature was achieved at a ramp rate of 10° C./minute.

Example 2

Preparation of Pt—Sn—Sr—Zn/γ-$Al_2O_3$ Catalyst (Catalyst B)

A Pt—Sn—Sr—Zn/γ-$Al_2O_3$ catalyst was prepared in a manner similar to example 1, with the difference that instead of dissolving 0.1450 g of $CaCl_2$, 0.1521 g of $SrCl_2$ was dissolved in 10 ml of DI water.

Example 3

Preparation of Catalysts for the Comparative Examples

A Pt—Sn/γ-$Al_2O_3$ catalyst (comparative catalyst C), Pt—Sn—Ca/γ-$Al_2O_3$ catalyst (comparative catalyst D), Pt—Sn—Zn/γ-$Al_2O_3$ catalyst (comparative catalyst E) were prepared in the same way as in example 1 with the difference that for comparative catalyst C, the solutions of $CaCl_2$ and $ZnCl_2$ were not used for comparative catalyst D, the solution of $ZnCl_2$ was not used for comparative catalyst E, the solution of $CaCl_2$ was not used.

Example 4

Preparation of Pt—Sn—Ca—Zn/ZSM-5 Catalyst

A Pt—Sn—Ca—Zn catalyst was prepared in a manner similar to example 1, with the difference that instead of γ-$Al_2O_3$, 5 g of a ZSM-5 zeolite support was used. The resulting Pt—Sn—Ca—Zn/ZSM-5 catalyst is hereafter referred to as comparative catalyst F.

Example 5

Testing of the Catalytic Activity of Catalysts A, B and Comparative Catalysts C, D, E and F The catalytic activity of the catalysts A, B and comparative catalysts C, D, E and F in propane dehydrogenation was measured in a quartz flow reactor having an internal diameter of 10 mm. To this end, 0.25-1.0 g catalyst was mixed with 1.0 g quartz sand (mesh size 12-25) and added to the quartz flow reactor. The reaction temperature was kept at 575° C. as measured by a thermocouple located in the catalyst bed. The feed stream contained $H_2$:propane:$N_2$ in a volume ratio of 1:1:5. The gas hourly space velocity (GHSV) of the feed stream was 3800.$h^{-1}$. The flow rate of the feed stream was controlled by mass flow controllers at the reactor inlet.

Before use, the catalysts were reduced in the reactor at a temperature of 575° C. for 2 hours.

The inlet and outlet composition of the reactants was analyzed by gas chromatograph SRI8610C (USA) with PID and HWD detectors. The reaction products were separated on a 2 m column filled with alkalinized alumina using nitrogen as a carrier gas.

The results of example 5 are presented in Table 1 below; wherein

Conv (%) is the conversion of propane in %.

Sel (%) is the selectivity of the catalyst towards propylene in the feed stream in %

Yield (%) is the selectivity towards propylene multiplied by the conversion of propane.

Carbon is the amount of carbon that is formed on the catalyst in mg/(g·h) as measured using TGA (thermogravimetric analysis).

TABLE 1

Catalytic activity data of from catalytic tests at feed composition of $H_2$:$C_3H_8$:N2 = 1:1:5, a GHSV of 3800 $h^{-1}$ and a temperature 575° C.

| Catalyst | Conv (%) | Sel (%) | Yield (%) | Cokes[1] | Product composition (mole %) | | | | |
|---|---|---|---|---|---|---|---|---|---|
| | | | | | $C_3H_8$ | $CH_4$ | $C_2H_6$ | $C_2H_4$ | $C_3H_6$ |
| A | 43.9 | 95.8 | 36.0 | 7.1 | 58.4 | 2.9 | 0.2 | 2.3 | 36.2 |
| B | 34.8 | 96.8 | 30.1 | 8.0 | 67.7 | 0.6 | 0.4 | 0.1 | 31.3 |
| C | 42.1 | 92.1 | 19.8 | 15.4 | 72.9 | 0.8 | 1.2 | 0.1 | 25.0 |
| D | 49.8 | 60.5 | 30.7 | 13.2 | 49.7 | 13.0 | 5.6 | 1.3 | 30.4 |
| E | 45.0 | 96.5 | 21.2 | 12.7 | 71.05 | 0.35 | 0.63 | 0.05 | 27.93 |
| F | 62.0 | 27.1 | 12.2 | 33.2 | 45.7 | 18.4 | 17.2 | 4.0 | 14.7 |

[1]The amount of cokes formed on the catalyst is given in mg · g cat$^{-1}$ · h$^{-1}$.

As can be seen from Table 1 above, propene is formed in a high yield when using the catalysts of the invention (catalysts A and B) as compared to comparative catalysts C—F. Also, the catalysts of the invention show a high selectivity towards propane. Furthermore, the amount of coke formed on the catalysts of the invention is lower.

This demonstrates the catalyst composition of the invention is capable of catalyzing the conversion of propane to propene in a non-oxidative dehydrogenation process in a high yield and with a high selectivity. It also demonstrates that the amount of coke formed on the catalyst in the catalyst composition of the invention may be lower. Also, the catalyst composition of the invention may be more stable for a longer Time on Stream (TOS).

Catalyst A has the further advantage that as a byproduct, relatively more ethylene is formed. This demonstrates that the total amount of valuable products that may be obtained in a non-oxidative dehydrogenation of propane is higher when using the catalyst according to the second special embodiment of the invention.

Set forth below are some embodiments of the catalyst composition, methods for making and using the catalyst composition.

Embodiment 1: A catalyst composition comprising: (a) a metal M selected from the group consisting of platinum (Pt), palladium (Pd), rhodium (Rh), rhenium (Re), ruthenium (Ru) and iridium (Ir); (b) tin (Sn); (c) zinc (Zn); (d) alkaline earth metal; and (e) a porous metal oxide catalyst support; wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support.

Embodiment 2: The catalyst composition according to Embodiment 1, wherein the alkaline earth metal is selected from the group consisting of magnesium (Mg), calcium (Ca) and strontium (Sr), preferably calcium (Ca).

Embodiment 3: The catalyst composition according to Embodiment 1 or Embodiment 2, wherein the metal M is platinum (Pt).

Embodiment 4: The catalyst composition according to any one of Embodiments 1-3, wherein the porous metal oxide catalyst support is selected from the group of γ-alumina (γ-$Al_2O_3$), titania ($TiO_2$), ceria ($CeO_2$), zirconia ($ZrO_2$) and mixtures thereof, preferably γ-alumina (γ-$Al_2O_3$).

Embodiment 5: The catalyst composition according to any one of Embodiments 1-4, wherein the porous metal oxide catalyst support has a BET surface area of 50-500 $m^2$/g.

Embodiment 6: The process for the preparation of a catalyst composition according to any one of Embodiments 1-5 comprising: (a) depositing the metal M, Sn, Zn and the alkaline earth metal on the porous metal oxide catalyst support to obtain a catalyst precursor; and (b) subjecting the catalyst precursor to calcination in an environment comprising oxygen to obtain a catalyst.

Embodiment 7: The process according to Embodiment 6, wherein step (a) comprises: (a1) contacting the porous metal oxide catalyst support with a solution comprising a salt of the metal M, a salt of tin (Sn), a salt of zinc (Zn) and a salt of the alkaline earth metal, and subsequently; (a2) evaporating the liquid in said solution to prepare a modified slurry; and (a3) washing the modified slurry with a solvent to obtain the catalyst precursor.

Embodiment 8: The process according to Embodiment 6 or 7, wherein calcination is performed at a temperature of 400 to 650° C. for 1 to 6 hours.

Embodiment 9: A catalyst composition, comprising: (a) a metal M selected from the group consisting of platinum (Pt), palladium (Pd), rhodium (Rh), rhenium (Re), ruthenium (Ru) and iridium (Ir); (b) tin (Sn); (c) zinc (Zn); (d) alkaline earth metal; and (e) a porous metal oxide catalyst support; wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support; wherein the catalyst composition is obtained or obtainable by a process comprising (a) depositing the metal M, Sn, Zn and the alkaline earth metal on the porous metal oxide catalyst support to obtain a catalyst precursor; and (b) subjecting the catalyst precursor to calcination in an environment comprising oxygen to obtain a catalyst; wherein step (a) comprises the steps of (a1) contacting the porous metal oxide catalyst support with a solution comprising a salt of the metal M, a salt of tin (Sn), a salt of zinc (Zn) and a salt of the alkaline earth metal, and subsequently; (a2) evaporating the liquid in said solution to prepare a modified slurry; and optionally (a3) washing the modified slurry with a solvent to obtain the catalyst precursor.

Embodiment 10: A process for producing an alkene by non-oxidative dehydrogenation of an alkane comprising the step of contacting a feed stream comprising the alkane with the catalyst composition of any one of Embodiments 1-5 and 9, to form the alkene.

Embodiment 11: The process according to Embodiment 10, wherein the alkane is propane.

Embodiment 12: The process according to Embodiment 10 or 11, wherein the non-oxidative dehydrogenation is performed at a temperature of from 400 to 650° C., a weight hourly space velocity of 0.1-1 hour$^{-1}$ and/or a pressure of 0.01-0.3 MPa.

Embodiment 13: A use of the catalyst composition of any one of Embodiments 1-5 or of Embodiment 9 in a non-oxidative dehydrogenation of an alkane.

The invention claimed is:

1. A catalyst composition comprising:
    (a) a metal M selected from the group consisting of platinum (Pt), palladium (Pd), rhodium (Rh), rhenium (Re), ruthenium (Ru) and iridium (Ir);
    (b) tin (Sn);
    (c) zinc (Zn);
    (d) alkaline earth metal; and
    (e) a porous metal oxide catalyst support;
wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support.

2. The catalyst composition according to claim 1, wherein the alkaline earth metal is selected from the group consisting of magnesium (Mg), calcium (Ca) and strontium (Sr).

3. The catalyst composition according to claim 1, wherein the metal M is platinum (Pt).

4. The catalyst composition according to claim 1, wherein the porous metal oxide catalyst support is selected from the group of γ-alumina (γ-Al$_2$O$_3$), titania (TiO$_2$), ceria (CeO$_2$), zirconia (ZrO$_2$) and mixtures thereof.

5. The catalyst composition according to claim 4, wherein the porous metal oxide catalyst support is γ-alumina (γ-Al$_2$O$_3$).

6. The catalyst composition according to claim 1, wherein the porous metal oxide catalyst support has a BET surface area of 50-500 m$^2$/g.

7. A process for the preparation of a catalyst composition according to claim 1 comprising:
    (a) depositing the metal M, Sn, Zn and the alkaline earth metal on the porous metal oxide catalyst support to obtain a catalyst precursor; and
    (b) subjecting the catalyst precursor to calcination in an environment comprising oxygen to obtain a catalyst, wherein step (a) comprises
        (a1) contacting the porous metal oxide catalyst support with a solution comprising a salt of the metal M, a salt of tin (Sn), a salt of zinc (Zn) and a salt of the alkaline earth metal, and subsequently;
        (a2) evaporating the liquid in said solution to prepare a modified slurry; and optionally (a3) washing the modified slurry with a solvent to obtain the catalyst precursor.

8. The process according to claim 7, wherein step (a) comprises:
    (a1) contacting the porous metal oxide catalyst support with a solution comprising a salt of the metal M, a salt of tin (Sn), a salt of zinc (Zn) and a salt of the alkaline earth metal, and subsequently;
    (a2) evaporating the liquid in said solution to prepare a modified slurry; and
    (a3) washing the modified slurry with a solvent to obtain the catalyst precursor.

9. The process according to claim 7, wherein calcination is performed at a temperature of 400 to 650° C. for 1 to 6 hours.

10. The process according to claim 7, wherein the solution has a pH in the range from 4 to 7.5.

11. The catalyst composition according to claim 1, wherein the alkaline earth metal is calcium (Ca).

12. The catalyst composition according to claim 1, wherein the amount of each of elements (a), (b) and (d) is independently chosen in the range of 0.5 to 2 wt %, based on the porous metal oxide catalyst support.

13. A catalyst composition, comprising:
    (a) a metal M selected from the group consisting of platinum (Pt), palladium (Pd), rhodium (Rh), rhenium (Re), ruthenium (Ru) and iridium (Ir);
    (b) tin (Sn);
    (c) zinc (Zn);
    (d) alkaline earth metal; and
    (e) a porous metal oxide catalyst support;
    wherein the amount of each of elements (a), (b) and (d) is independently chosen in the range of from 0.1 to 5 wt. % based on the porous metal oxide catalyst support and wherein the amount of element (c) is chosen in the range of from 0.1 to 2 wt. % based on the porous metal oxide catalyst support;
    wherein the catalyst composition is obtained by a process comprising
        (a) depositing the metal M, Sn, Zn and the alkaline earth metal on the porous metal oxide catalyst support to obtain a catalyst precursor; and
        (b) subjecting the catalyst precursor to calcination in an environment comprising oxygen to obtain a catalyst;
        wherein step (a) comprises the steps of
            (a1) contacting the porous metal oxide catalyst support with a solution comprising a salt of the metal M, a salt of tin (Sn), a salt of zinc (Zn) and a salt of the alkaline earth metal, and subsequently;
            (a2) evaporating the liquid in said solution to prepare a modified slurry; and
            optionally (a3) washing the modified slurry with a solvent to obtain the catalyst precursor.

14. A process for producing an alkene by non-oxidative dehydrogenation of an alkane comprising the step of contacting a feed stream comprising the alkane with the catalyst composition of claim 1 to form the alkene.

15. The process according to claim 14, wherein the alkane is propane.

16. The process according to claim 14, wherein the non-oxidative dehydrogenation is performed at a temperature of from 400 to 650° C., a weight hourly space velocity of 0.1-1 hour$^{-1}$ and/or a pressure of 0.01-0.3 MPa.

17. A process for producing an alkene by non-oxidative dehydrogenation of an alkane comprising the step of contacting a feed stream comprising the alkane with the catalyst composition of claim 13 to form the alkene.

18. The catalyst composition according to claim 13, wherein the solution has a pH in the range from 4 to 7.5.

\* \* \* \* \*